United States Patent [19]

Klein

[11] 4,149,013
[45] Apr. 10, 1979

[54] PROCESS FOR PURIFYING 1,12-DODECANEDIOIC ACID

[75] Inventor: David A. Klein, Wilmington, N.C.

[73] Assignee: E. I. Du Pont de Nemours and Company, Wilmington, Del.

[21] Appl. No.: 907,824

[22] Filed: May 19, 1978

[51] Int. Cl.$^2$ ............................................. C07C 51/42
[52] U.S. Cl. ..................................................... 562/593
[58] Field of Search .............................. 562/593, 590

[56] References Cited

U.S. PATENT DOCUMENTS

| | | | |
|---|---|---|---|
| 2,847,467 | 8/1958 | Steadman et al. | 562/593 |
| 3,417,138 | 12/1968 | Amir et al. | 562/593 |
| 3,714,244 | 1/1973 | Okada et al. | 562/593 |
| 3,903,152 | 9/1975 | Matsubara et al. | 562/593 |

Primary Examiner—Vivian Garner

[57] ABSTRACT

Process for purifying 1,12-dodecanedioic acid "DDA" by dissolving the impure DDA in hot aqueous acetic acid in the presence of phosphoric acid and a compound containing peroxidic oxygen (e.g., hydrogen peroxide, peracetic acid); filtering the solution to remove insoluble materials, e.g., iron phosphate; cooling the filtrate to recrystallize the DDA; washing the recrystallized DDA with aqueous acetic acid and then with water; and recovering the washed DDA crystals. This purified DDA is suitable for conversion into polyamide textile fiber.

5 Claims, 1 Drawing Figure

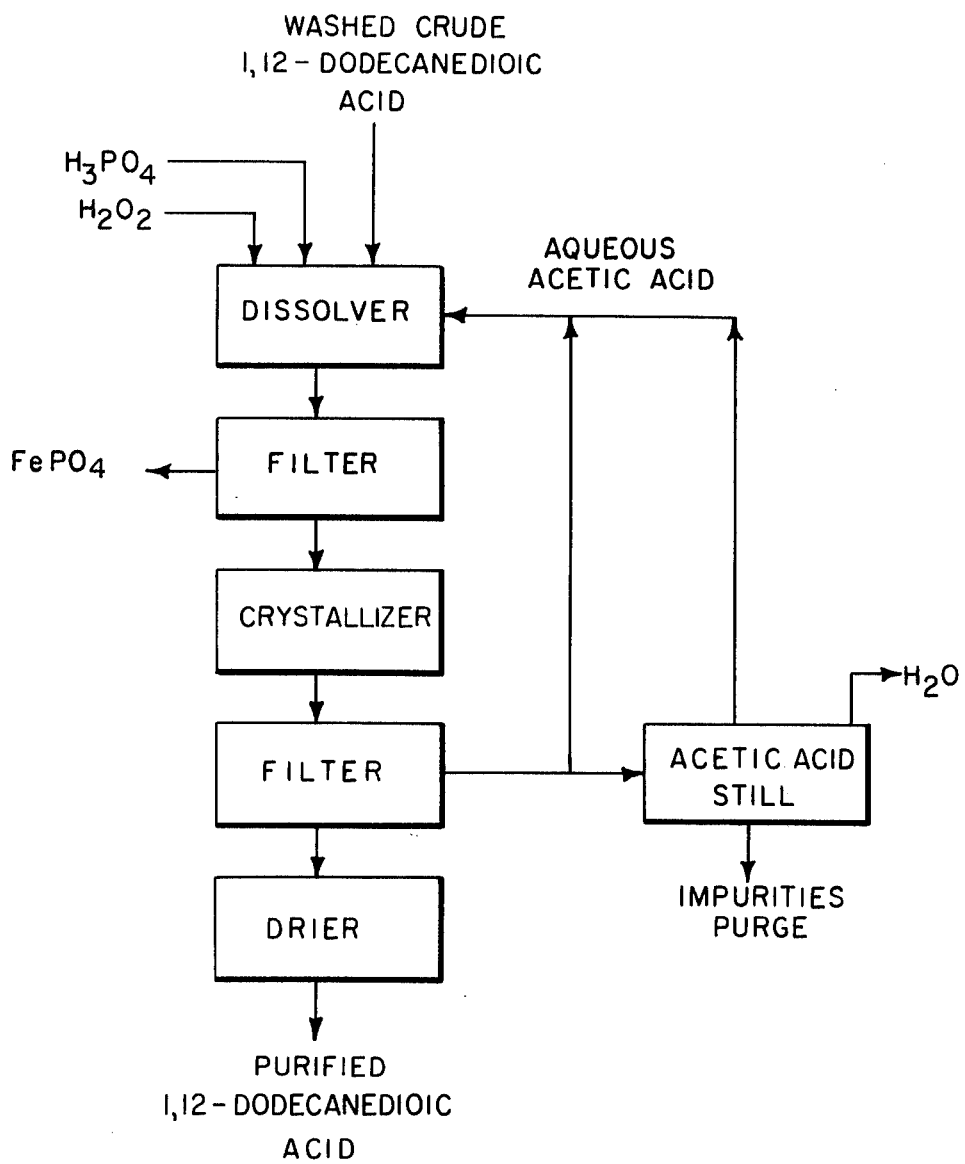

PROCESS FOR PURIFYING 1,12-DODECANEDIOIC ACID

BACKGROUND OF THE INVENTION

This invention concerns the purification of 1,12-dodecanedioic acid that contains iron and other color-forming impurities.

U.S. Pat. No. 2,601,233 discloses that 1,12-dodecanedioic acid can be produced by a reductive coupling treatment of an organic peroxide, such as the addition product obtained by the reaction of cyclohexanone and hydrogen peroxide, with an appropriate reducing agent, such as ferrous iron compound. Such a treatment is referred to herein as an "iron-reductive-coupling step." According to U.S. Pat. No. 3,907,883, an iron-reductive-coupling step can be carried out by a process in which a solution of the organic peroxide in a suitable organic solvent is thoroughly mixed with an aqueous solution of a chelated ferrous iron compound, to form the desired dodecanedioic acid by reductive coupling of the organic peroxide and oxidation of the chelated ferrous iron to the ferric state. Two phases are formed in the mixture; an organic solvent phase which contains the desired 1,12-dodecanedioic acid product and an aqueous phase which contains the oxidized or spent reductant solution. The two phases can be separated quite readily, for example by decantation. It is suggested that the dodecanedioic acid product can then be recovered by crystallization from the organic layer or the organic solvent can be steam-distilled and the desired product crystallized from the aqueous tails.

The dodecanedioic acid recovered from the above-described processes is useful, for example, for conversion into polyamides or in the manufacture of plastics. However, it has been found that undesirable quantities of iron and color-forming organic impurities are often present in the acid. Such impurities are detrimental, especially when the dodecanedioic acid is to be converted to polyamide polymers intended for the manufacture of high-quality textile fibers and filaments.

SUMMARY OF THE INVENTION

The present invention provides a method for purifying 1,12-dodecanedioic acid that contains iron and organic color-forming impurities, such as 1,12-dodecanedioic acid that is produced by a process which includes an iron-reductive-coupling step. The purification process comprises forming a solution at a temperature of 70° to 125° C. of crude dodecanedioic acid in water, acetic acid, phosphoric acid and a compound containing peroxidic oxygen; filtering the hot solution to remove insoluble materials; cooling the filtrate to a temperature in the range of 5° to 65° C. to recrystallize the 1,12-dodecanedioic acid; washing the recrystallized 1,12-dodecanedioic acid with aqueous acetic acid at a temperature of between 10 and 50° C. and then with water; and recovering the treated acid.

DESCRIPTION OF THE DRAWING

The attached drawing is a flowsheet of an embodiment of a continuous process of the present invention.

DETAILED DESCRIPTION OF THE INVENTION

The starting material for the process of the present invention is 1,12-dodecanedioic acid (hereinafter referred to as "DDA") in a crude state containing color-forming impurities, such as iron and various organic by-products. Crude DDA is produced by known processes using iron-reductive-coupling. Typically, for crude DDA made by the methods of U.S. Pat. No. 3,907,883, iron impurity concentrations of 20 to 30 ppm are present and the crude DDA has a "b" color (as hereinafter defined) of 5 to 15. However, if process upsets or unusual operating conditions are experienced in the DDA manufacturing process, the crude DDA can have an iron content of 50 ppm or more and "b" color values of 25 or more. By the process of the present invention, the concentration of iron and other color-forming impurities are reduced to such an extent that the purified DDA is satisfactory for conversion to polyamides intended for use as high quality textile fibers. Generally, the purified DDA contains less than 1 ppm of iron and has a "b" color of less than 1, often as low as zero. It is preferred, prior to subjecting the crude DDA to the purification process of the present invention to wash the DDA with cyclohexane and then with water to remove cyclohexane-soluble and water-soluble impurities that may be present from the DDA manufacturing process.

The purification process of the present invention involves five main steps:

(1) dissolving the crude DDA to form a solution containing specific materials;

(2) filtering the solution;

(3) recrystallizing the DDA;

(4) washing sequentially with aqueous acetic acid and water; and (5) recovering purified DDA. If necessary, especially when purifying excessively contaminated crude DDA produced during process upsets, the purification steps can be repeated.

In the dissolution step, the crude DDA is dissolved in hot aqueous acetic acid. Small quantities of phosphoric acid and a compound containing peroxidic oxygen are included in the solution. Generally, a temperature in the range of 70° to 125° C. is suitable, but a temperature of 90° to 100° C. is preferred. Usually the solution contains 30 to 70% by weight acetic acid, with 40 to 50% being preferred. The concentration of DDA in the solution is usually no more than the solubility limit of the DDA at the solution temperature. For example, the approximate solubility of DDA in the solution at 70° C. is only about 3% and at 105° C. is about 25%. In the preferred 90°-to-100° C. temperature range, the DDA concentration is about 15 to 20%. All percentages are based on the total weight of the solution.

The presence of phosphoric acid in the solution causes the formation and subsequent precipitation of insoluble phosphates, principally iron phosphate. The quantity of phosphoric acid present in the solution is generally in excess of the stoichiometric amount required to precipitate all the iron impurities as iron phosphate, usually at least four times the stoichiometric amount, perferably more than ten times. Many times the stoichiometric amount can be used, for example, between 50 and 200 times.

To assist in removal of color-forming impurities, the DDA solution in acetic acid, in addition to phosphoric acid, also includes a compound which contains a peroxidic oxygen or which forms peroxidic oxygen in the system i.e., in the presence of water, acetic acid or mixtures thereof. The peroxidic-oxygen-containing compound can be formed in situ, as for example by adding an aldehyde, such as acetaldehyde, and air to the solution. Examples of suitable peroxides include inorganic peroxides such as $Na_2O_2$, $K_2O_2$, $BaO_2$, $MgO_2$, $NaBO_3.4H_2O$, and $K_2C_2O_6$; hydrogen peroxide addition compounds such as sodium carbonate peroxyhydrate ($Na_2CO_3.1.5H_2O_2$); superoxides such as $KO_2$ and $NaO_2$; organic peroxides such as hydroperoxides, peroxyacids and peroxyesters exemplified by $CH_3OOH$, cyclohexylhydroperoxide, and tetralin hydroperoxide, perbenzoic acid, peracetic acid and perpropionic acid. Additional peroxides are disclosed in Kirk-Othmer *Encyclopedia of Chemical Technology*, 2nd Edition, Vol. 14, 746–834, (1976). As one skilled in the art appreciates, the peroxide should not react with the DDA or solubilize the iron compounds. Peroxides selected from the group consisting of hydrogen peroxide, peracetic acid and mixtures thereof are preferred. Generally, a mole ratio of peroxidic oxygen to DDA of between 0.01:1 and 0.3:1 has been found suitable for use in the present process; mole ratios of 0.05:1 to 0.1:1 are preferred.

The solution is generally maintained at temperature for between 10 minutes and 2 hours. Although longer times at temperature give satisfactory results, for practical or economical reasons, minimum holding times, e.g., times of 15 to 45 minutes are preferred.

As noted above, in the dissolution of the crude DDA, three ingredients are necessary: (1) aqueous acetic acid solvent; (2) phosphoric acid; and (3) a compound containing peroxidic oxygen. When aqueous acetic acid is used alone in the process, the resulting iron content and the "b" color in the treated DDA are at undesirably high levels in the final DDA product. The addition of phosphoric acid to the dissolution step, but without the peroxidic oxygen compound, in some cases reduces the iron content to a satisfactory level but does not consistently provide the needed reduction in "b" color. The addition of a peroxidic oxygen compound (e.g., hydrogen peroxide) to the dissolution step, in the absence of phosphoric acid, does not permit a satisfactory reduction in either the iron content or the "b" color of the DDA. However, the beneficial effect of adding both phosphoric acid and a peroxidic oxygen compound to the dissolution step, in accordance with the present invention, apparently is synergistic. Surprisingly, both the iron content and "b" color of the DDA when initially present at normal levels are reduced to sufficiently low levels that the purified DDA is consistently suitable for conversion to polyamides intended for the manufacture of high-quality textile fibers.

Insoluble material, principally iron phosphate, that was formed by the reaction of the phosphoric acid is separated from the hot solution before the DDA is crystallized. This separation usually is conducted with the solution at about the same temperature as in the dissolution to avoid premature recrystallization of the DDA. Filtration is the preferred method of separation in this step.

The filtrate containing the dissolved DDA is cooled, generally to a temperature of between 5° and 65° C., preferably between 40° to 50° C., to recrystallize the DDA. The recrystallized DDA can be readily removed from the cooled liquid by filtration, centrifugation, or the like. To remove any residual impurities, the DDA crystals are washed at a temperature between 10° and 50° C. with aqueous acetic acid, then with water and dried.

The cooled acetic acid liquid from which the purified DDA crystals are recovered can be recycled to the dissolution step. The attached drawing shows a schematic flow sheet of a continuous DDA purification process wherein the acetic acid is recycled. In the continuous process, crude DDA, preferably prewashed with cyclohexane and water, is fed to a dissolver along with the desired quantities of 50% aqueous acetic acid, phosphoric acid and the compound containing peroxidic oxygen, which in the flow sheet is hydrogen peroxide. The contents of the dissolver are thoroughly mixed and maintained at a temperature of about 95° C. for about 30 minutes. The effluent from the dissolver is then passed hot through the filter, which removes insoluble materials, e.g., iron phosphate from the solution. The filtrate is forwarded to a crystallizer where the temperature is lowered to about 45° C. The crystallizer effluent is then filtered to form a cake of DDA crystals. The cake is then washed at a temperature of about 30° C., first with aqueous acetic acid and then with water. The DDA crystals, which are now in a purified state, are then dried and recovered. A major portion of the acetic acid filtrate from the last filter is recycled directly to dissolver. The remaining portion of the acetic acid, prior to recycling, is fed to a still which is used for adjusting the acetic acid concentration and for purging impurities.

As used herein, "b" color refers to a measure of the color-forming impurity content of the DDA and correlates with the ultimate color of polyamides prepared from the DDA. The "b" color of the DDA is determined by reflectance measurements made according to the general procedure of ASTM-1925-63-T on solid cakes cast from molten DDA. The iron impurity concentrations are determined by burning a 50-gram sample of DDA to an ash, dissolving the ash, contacting the solution with hydroxylamine hydrochloride, adding excess 1,10-phenanthroline to form a colored solution of ferrous ortho-phenanthroline, and then determining the iron concentration by spectrophotometric analysis of the solution.

The following examples are presented to illustrate, but not to limit, the present invention. Parts and percentages are by weight unless otherwise specified. In each of the examples, the crude DDA was manufactured by the general procedure of U.S. Pat. No. 3,907,883 and washed at about 20° C., first with cyclohexane and then water, prior to being subjected to purification treatment. In Examples I, II, and III, the washed crude DDA, which was tan in color, contained about 20 to 25 ppm of iron, had an average "b" color of about 15, and, as shown by gas-chromatographic analysis, contained 62.8% dodecanedioic acid, 0.52% caproic acid, 0.12% 5-hexanoic acid and 0.11% cyclohexane, with water and trace quantities of cyclohexane and unidentified by-products accounting for the remainder. The washed crude DDA of Example IV was reddish brown in color, contained about 50 ppm of iron, had a "b" color of 25, and contained about 60% DDA. Example IV is included to show the suitability of the present process in purifying excessively contaminated DDA made during upsets of the iron-reductive-coupling step of the DDA manufacturing process.

EXAMPLE I

A 1000-ml, round-bottom, three-neck flask, equipped with a reflux condenser, a magnetic stirrer, a thermometer and a heating mantle initially was charged with 200 grams of glacial acetic acid and 200 grams of distilled demineralized water and heated to 100° C. The following were then added to the flask:

35 ml of glacial acetic acid (36.7 grams);
111.5 grams of washed crude DDA (0.304 mole of DDA);
0.5 ml of 85% phosphoric acid (0.008 mole $H_3PO_4$);
3 ml of 30% aqueous hydrogen peroxide (0.03 mole $H_2O_2$).

The iron impurity content amounted to between $4 \times 10^{-5}$ and $5 \times 10^{-5}$ gram mole.

The contents of the flask were stirred and maintained at 100° C. for an hour and then filtered at approximately 100° C. through a steam-jacketed fritted-disc filter under 3.5-kg/cm²-gage nitrogen to remove precipitate. The resulting filtrate was reheated to redissolve any DDA that had begun to crystallize. Then, the filtrate was slowly stirred and cooled to 45° C. to recrystallize the dodecanedioic acid, after which the crystals were separated from the liquid by filtration. The filtrate from this separation weighed 412 grams and was saved for recycle tests described below in Example II. The filter cake was washed twice with 150 ml of 50% aqueous acetic acid and then twice with 150 ml of distilled demineralized water. The cake was then dried in air for 20 minutes and further dried at 100° C. in a vacuum drying oven for about 16 hours. The refined dried DDA product weighed 66.4 grams (i.e., about a 95% yield), had a "b" color of 0.1 and contained 0.23 ppm of iron.

For the purposes of comparison an identical experiment was run, as above, except that no hydrogen peroxide was added to the flask. In this comparative test the dried DDA product weighed 65.5 grams, had a "b" color of 1.0 and contained 0.88 ppm of iron.

As an additional comparison, the above-described procedure for the process of the invention was repeated except that no phosphoric acid was added and the contents of the flask were maintained at 100° C. for 30 minutes. The dried DDA recovered from this test without phosphoric acid, weighed 65.1 grams, had a "b" color of 1.33 and an iron content of 2.1 ppm. In a second identical test without phosphoric acid, except that 133.8 grams of washed crude DDA were treated, 79.9 grams of dried DDA were recovered having a "b" color of 1.35 and an iron content of 2.6 ppm.

EXAMPLE II

In the following series of recycle tests, the procedure of Example I was repeated except that for recycle test 1, the 200 grams of glacial acetic acid and 200 grams of distilled demineralized water were replaced by the filtrate saved in Example I for recycle tests and in all subsequent recycle tests, the filtrate from the preceding test was used. The acetic acid concentration in the recycle liquid was 51 to 58%. For comparison, a second series of recycle tests was run in the same way, except that the addition of hydrogen peroxide was omitted. The results are summarized in Table I, which shows the superiority of the purification process of the present invention over a process run in the same manner, but without hydrogen peroxide being present in the solution.

TABLE I

| | Purification Tests with Recycled Acetic Acid | | | | | |
|---|---|---|---|---|---|---|
| | According to Invention With $H_2O_2$ Addition | | | Comparison Test-No $H_2O_2$ Addition | | |
| Recycle Test No. | Recovered DDA (Grams) | "b" Color | ppm Fe | Recovered DDA (Grams) | "b" Color | ppm Fe |
| 1 | 70.3 | 0.7 | 0.23 | 63.3 | 3.0 | 0.88 |
| 2 | 67.2 | 0.0 | 0.65 | 68.2 | 2.5 | 1.28 |
| 3 | 67.6 | 0.0 | 0.38 | 69.7 | 3.3 | 0.13 |
| 4 | 67.2 | 0.0 | 0.65 | 66.4 | 2.7 | 0.38 |
| 5 | 66.5 | 0.0 | 1.13 | 67.5 | 3.3 | 0.13 |
| 6 | 66.9 | 0.0 | 0.95 | 68.8 | 3.0 | 0.18 |
| 7 | 65.8 | 0.0 | 0.08 | 68.3 | 3.5 | 0.0 |

Recycle acetic acid from the seventh recycle test carried out in accordance with the invention, was used as starting solvent for an additional eleven subsequent sequential recycle tests in which 133.8 grams of washed crude DDA were treated as above, except that the hold-up time in dissolution was only 15 minutes. Acid concentrations in these additional recycle tests, calculated as % acetic acid, were 38 to 54%. The dried, recovered DDA in each of these tests weighed between 80.9 and 84.4 grams, had a "b" color of 0 to 0.44 (except for one product which had a "b" color of 0.9) and contained between 0.08 and 1.00 ppm of iron.

Acetic acid recovered from the eleventh of the above-described additional recycle tests were used as the starting solvent in still another four sequential recycle tests, run in the same way as the preceding eleven recycle tests, except that the hold-up time in dissolution was ½ hour. The dried recovered DDA in each of these tests weighed between 81.8 and 84.8 grams, had "b" colors of 0 and 0.3 and contained 0.46, 1.55, 0 and 0.35 ppm of iron, respectively.

EXAMPLE III

The procedure of Example I was repeated except that 133.8 grams of washed crude DDA were used, 5 milliliters of 40% peracetic acid in acetic acid were substituted for the aqueous hydrogen peroxide, the temperature of dissolution was 95° C. and the hold-up time in dissolution was 30 minutes. As a result of this treatment 81.8 grams of refined dried DDA were recovered having a "b" color of 0 and containing 1.1 ppm of iron. A recycle test, using acetic acid recovered from the final filtration, but in all other conditions the same as this just-described test, resulted in 83.2 grams of dried refined DDA having a "b" color of 0.15 and an iron content of 0.9 ppm.

EXAMPLE IV

This example shows the use of the process of the present invention for refining very poor quality crude DDA.

The procedure of Example I was repeated, four times, except that 133.8 grams of washed crude DDA having a reddish color were used each time. Heating times for the solution and the amounts of 85% phosphoric acid and 30% aqueous hydrogen peroxide were as follows:

| | | | Recovered DDA | | |
|---|---|---|---|---|---|
| ml $H_3PO_4$ | ml $H_2O_2$ | Hours at 100° S. | Grams (Dry) | "b" Color | ppm Fe |
| 0.5 | 3 | 0.5 | 61.7 | 1.8 | 0.6 |
| 0.5 | 3 | 0.5 | 65.7 | 2.6 | 0.5 |

-continued

| ml H3PO4 | ml H2O2 | Hours at 100° S. | Recovered DDA Grams (Dry) | "b" Color | ppm Fe |
|---|---|---|---|---|---|
| 1 | 6 | 1 | 62.0 | 3.9 | 0.9 |
| 2 | 6 | 2.5 | 60.7 | 2.6 | 0.5 |

The once-refined recovered dry DDA crystals from the four above-described runs were combined and mixed. A 90-gram sample of the mixture was refined again with fresh 50% aqueous acetic acid by the procedure of the invention as described in Example I, except that the extra 35 milliliters of glacial acetic acid were omitted and 1 milliliter of 85% phosphoric acid, 6 milliliters of 30% aqueous hydrogen peroxide and 1-hour hold-up time at 100° C. were used. The twice-refined dried DDA product weighed 82.8 grams, contained less than 0.5 ppm of iron and had a "b" color of 1.0.

I claim:

1. A method for purifying crude 1,12-dodecanedioic acid produced by a process that includes an iron-reductive-coupling step and contains color-forming impurities including iron, comprising forming a solution at a temperature of 70° to 125° C. comprising dissolved crude 1,12-dodecanedioic acid, water, acetic acid, phosphoric acid and a compound containing peroxidic oxygen;

separating insoluble material from said solution;

cooling the solution to a temperature in the range of 5° to 65° C. to recrystallize the 1,12-dodecanedioic acid;

washing the recrystallized 1,12-dodecanedioic acid at a temperature between 10° and 50° C., with aqueous acetic acid and then with water; and recovering the thus treated 1,12-dodecanedioic acid.

2. The method of claim 1, wherein the solution contains between 30 and 70 weight percent acetic acid, a quantity of phosphoric acid that is in excess of the stoichiometric amount required to convert the iron in the crude 1,12-dodecanedioic acid to iron phosphate, and a quantity of peroxidic-oxygen compound that provides a mole ratio of peroxidic oxygen to 1,12-dodecanedioic acid of between 0.01:1 and 0.3:1 and the solution is maintained at 70°–125° C. for between 10 minutes and two hours.

3. The method of claim 2, wherein the peroxidic-oxygen compound is selected from the group consisting of hydrogen peroxide, peracetic acid and mixtures thereof and is present in an amount sufficient to provide a mole ratio of peroxidic oxygen to 1,12-dodecanedioic acid of between 0.05:1 to 0.1:1, the solution is maintained at a temperature in the range of 90°–100° C. for 15 to 45 minutes, and the recrystallization temperature is in the range of 40° to 50° C.

4. The method of claim 1, wherein the crude 1,12-dodecanedioic acid is washed sequentially with cyclohexane and water before it is placed in solution.

5. The method of claim 1, wherein at least a portion of the solution from which the 1,12-dodecanedioic acid has been recrystallized is recycled to the solution-forming step.

* * * * *